United States Patent [19]

Leder et al.

[11] 3,946,088

[45] Mar. 23, 1976

[54] HYDROCARBON ISOMERIZATION PROCESS

[75] Inventors: Frederic Leder, South Orange; George M. Kramer, Berkeley Heights, both of N.J.; Herman J. Solomon, Milford, Conn.

[73] Assignee: Exxon Research & Engineering Co., Linden, N.J.

[22] Filed: Oct. 11, 1974

[21] Appl. No.: 514,002

[52] U.S. Cl. .......................... 260/683.75; 260/666 P
[51] Int. Cl.² ............................................ C07C 5/28
[58] Field of Search ......... 260/683.7, 683.75, 666 P

[56] References Cited
UNITED STATES PATENTS

| | | | |
|---|---|---|---|
| 2,250,410 | 7/1941 | van Peski | 260/683.7 |
| 2,265,548 | 12/1941 | Schuit | 260/683.75 |
| 2,271,043 | 1/1942 | van Peski | 260/683.75 |
| 2,992,285 | 7/1961 | Arey, Jr. et al. | 260/683.75 |
| 3,201,496 | 8/1965 | Hill | 260/683.7 |

FOREIGN PATENTS OR APPLICATIONS

| | | | |
|---|---|---|---|
| 764,704 | 11/1952 | Germany | 260/683.7 |

*Primary Examiner*—Delbert E. Gantz
*Assistant Examiner*—G. J. Crasanakis
*Attorney, Agent, or Firm*—M. L. Gibbons

[57] ABSTRACT

A hydrocarbon feed is isomerized in liquid phase in the presence of a metal halide catalyst, a hydrogen halide solvent and hydrogen at a temperature ranging from at least 50°C and not greater than the critical temperature of the mixture of the hydrocarbon feed and the hydrogen halide. The partial pressure of the hydrocarbon feed-hydrogen halide mixture is maintained to be at least equal to the critical pressure of the hydrocarbon feed and not greater than the critical pressure of the mixture of the hydrocarbon feed and the hydrogen halide. The molar ratio of the hydrogen halide to the hydrocarbon feed is at least 1:1 and the molar ratio of hydrogen halide to metal halide catalyst ranges from about 10:1 to about 40:1. The preferred catalyst is aluminum chloride or aluminum bromide. The preferred solvent is hydrogen chloride or hydrogen bromide.

16 Claims, 3 Drawing Figures

THE CRITICAL LOCI OF HCL-HYDROCARBON MIXTURE

THE CRITICAL LOCI OF HBr-HYDROCARBON MIXTURE

HYDROCARBON ISOMERIZATION PROCESS

BACKGROUND OF THE INVENTION

1. Field of the Invention

The present invention relates to a process for the conversion of hydrocarbons. More particularly, this invention relates to a catalytic process for the isomerization of saturated aliphatic hydrocarbons.

2. Description of the Prior Art

It is known that aliphatic hydrocarbons can be isomerized in processes involving the use of a metal halide catalyst and a hydrogen halide in the presence or absence of hydrogen. Furthermore, it is known that isomerization can be conducted below the critical temperature of the hydrogen halide at substantially liquid phase conditions.

German patent No. 764,704 discloses that it is beneficial to use at least 100 weight percent of hydrogen halide to hydrocarbon feed in the isomerization zone to suppress cracking. It further discloses that temperatures in the range of 50° to 150°C may be used.

U.S. Pat. No. 2,250,410 discloses an isomerization process conducted in the presence of a metal halide catalyst at a temperature of 20° to 150°C under a superatmospheric pressure, the total pressure in the system being sufficiently high to insure the presence of a liquid phase of hydrocarbon in the system and the partial pressure of a hydrogen halide in the system being equivalent to 3 to 20 atmospheres when measured at 20°C.

U.S. Pat. No. 2,271,043 discloses an isomerization which may be conducted in liquid or gaseous phase at a temperature below 200°C in the presence of a hydrogen halide promoter and between 0.08 and 33 atmospheres of added hydrogen to repress undesired side reactions.

It has now been found that superior isomerization results can be obtained when the isomerization is conducted at pressure and temperature conditions comprised within the area (with reference to a pressure-temperature plot) bounded by the loci of the critical constants of mixtures of the hydrogen halide and hydrocarbon feed, at a specified ratio of hydrogen halide to metal halide catalyst, in the presence of added hydrogen.

SUMMARY OF THE INVENTION

In accordance with the invention, there is provided an isomerization process which comprises: contacting, in a reaction zone, in the presence of hydrogen, a hydrocarbon feed comprising a saturated aliphatic hydrocarbon, a hydrogen halide selected from the group consisting of hydrogen chloride, hydrogen bromide and mixtures thereof, said hydrocarbon feed and said hydrogen halide being substantially in liquid phase, and a metal halide catalyst selected from the group consisting of metal chlorides, metal bromides and mixtures thereof, at a temperature ranging from at least about 50°C to the critical temperature of the mixture of said hydrocarbon feed and said hydrogen halide, the partial pressure of the mixture of said hydrocarbon feed and said hydrogen halide being maintained at least equal to the critical pressure of the hydrocarbon feed and not greater than the critical pressure of said mixture of hydrocarbon feed and hydrogen halide, and wherein the molar ratio of said hydrogen halide to said hydrocarbon feed is at least 1:1, and the molar ratio of said hydrogen halide to said metal halide catalyst ranges from about 10:1 to about 40:1.

DESCRIPTION OF THE PREFERRED EMBODIMENT

Figure 1:
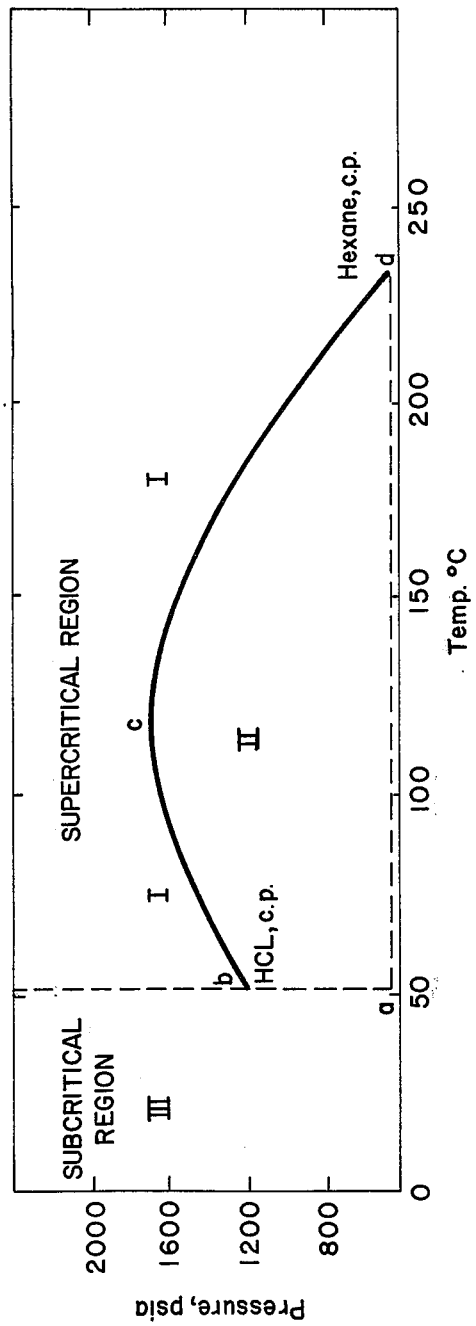
FIG. 1 is a plot showing the critical temperature and pressure of mixtures of varying proportions of hydrogen chloride and n-hexane.

The isomerization process of the present invention is effective for converting saturated acyclic aliphatic hydrocarbons having at least 4 carbon atoms and alicyclic aliphatic hydrocarbons having at least 6 carbon atoms, to a product enriched in an isomer thereof. Typically, acyclic hydrocarbons, that is, straight chain or branched chain paraffins having from about 4 to 10 carbon atoms, preferably from about 4 to 7 carbon atoms are converted to branched chain materials having higher octane ratings. Alicyclic hydrocarbons (naphthenes) having typically from about 6 to 15 carbon atoms, preferably from about 6 to 9 carbon atoms can be converted to isomers thereof.

The feedstock may comprise individual acyclic hydrocarbons or mixtures thereof, individual alicyclic hydrocarbons or mixtures thereof, or mixtures of acyclic and alicyclic hydrocarbons. Typically, mixtures of saturated alicyclic aliphatic hydrocarbons and saturated acyclic aliphatic hydrocarbons are used as feed.

Suitable metal halide catalysts for use in the process of the invention are metal chlorides and metal bromides, for example, aluminum chloride, aluminum bromide, gallium trichloride, gallium tribromide, zinc chloride, ferrous chloride, ferric chloride, zirconium chloride, stannic chloride, boron tribromide, boron trichloride, etc. The preferred metal halide catalyst is aluminum chloride or aluminum bromide. If desired, promoters such as water or methyl t-amyl ether may be used in addition to the metal halide. The amount of metal halide catalyst present in the reaction zone is not critical. Typically, from about 0.02 to 2.0, preferably from 0.1 to 0.5 weight parts of metal halide are present in the reaction zone per weight part of hydrocarbon reactant.

The metal halide is used in combination with a hydrogen halide solvent comprising hydrogen chloride, hydrogen bromide or mixtures thereof. Desirably, the halide moiety of the hydrogen halide and of the metal halide catalyst are the same to avoid exchange reactions.

The molar ratio of hydrogen halide to metal halide catalyst utilized in the isomerization reaction ranges from about 10:1 to about 40:1, preferably from about 20:1 to about 40:1.

The molar ratio of hydrogen halide to hydrocarbon feed is at least 1:1, preferably from about 2:1 to about 10:1.

The isomerization reaction of the present invention is conducted in the presence of molecular hydrogen. Hydrogen, derived from any suitable source, may be added to the reaction zone, or the hydrogen may be generated in situ by introducing hydride donors into the reaction zone during the course of the reaction. Examples of useful hydride donors include decalin, tetralin, methylcyclohexane and the like. Most preferably, molecular hydrogen is introduced into the isomerization zone. Sufficient hydrogen is maintained in the isomerization zone to provide a partial pressure of at least 15 pounds per square inch absolute (psia). Suitable hydrogen partial pressure in the reaction zone will range from about 15 to about 2000 psia, preferably from about 40 to about 1000 psia, more preferably from about 40 to about 400 psia.

Typically, from 0.05 to 2.5 moles, preferably from 0.05 to 1 mole of $H_2$ per mole of hydrocarbon feed are present in the reaction zone. In a typical reaction system, the isomerization is permitted to proceed for time periods varying from about 0.5 to 1500, preferably from about 1 to 500 minutes.

Generally, the higher hydrogen partial pressures are utilized with the higher isomerization temperatures and the lower hydrogen partial pressures are utilized with the lower isomerization temperatures. In a typical refinery operation, the hydrocarbon feedstock, hydrogen halide and hydrogen are admixed with the metal halide catalyst in a substantially liquid phase operation. The contacting may be carried out in a plurality of serially connected mixing zones. Since liquid HCl and HBr are very miscible with hydrocarbons, a product stream is withdrawn from the reaction zone and separated by utilizing conventional distillation techniques. Optionally, the metal halide catalyst may be impregnated on an inert (to the hydrogen halide) porous support material and the hydrocarbon feedstock and hydrogen halide, in substantially liquid phase, passed over the supported metal halide catalyst.

The liquid phase isomerization is conducted at a temperature ranging from at least about 50°C, preferably at a temperature at least as great as the critical temperature of the hydrogen halide used in the reaction zone to the critical temperature of the mixture of the hydrocarbon feed and hydrogen halide.

In general, suitable isomerization reaction temperatures will be comprised within the range from about 50° to about 150°C, preferably from about 60° to about 125°C, more preferably from about 65° to 110°C, depending on the specific hydrogen halide solvent and hydrocarbon feed used.

The partial pressure of the mixture of hydrocarbon feed and hydrogen halide is maintained to range from a pressure at least as great as the critical pressure of the hydrocarbon feed and not greater than the critical pressure of the mixture of the hydrocarbon feed and hydrogen halide. In general, the partial pressure of the hydrocarbon feed-hydrogen halide mixture will range from about 250 to about 2500 psia. It is to be noted that by partial pressure of the mixture is intended herein the partial pressure of the hydrocarbon feed and hydrogen halide alone, that is, excluding the partial pressure of hydrogen. The total pressure, including the hydrogen partial pressure, in the isomerization zone will range broadly from about 265 to about 3000 psia, preferably from about 300 to about 2700 psia.

The critical temperature and the critical pressure of a mixture of hydrocarbon feed and hydrogen halide can be estimated in accordance with the expressions:

$$T_c' = \Sigma_i x_i (T_c)_i$$

$$P_c' = \Sigma_i x_i (P_c)_i$$

wherein $x_i$ is the mole fraction of the ith chemical species, as shown in *Molecular Theory of Gases and Liquids*, J. O. Hirschfelder, C. F. Curtiss, and R. D. Bird, p. 244, New York: John Wiley and Sons (1954).

The critical temperature of a mixture can also be determined experimentally by introducing the mixture in a high pressure sight glass with variable volume or pressurizing equipment and slowly varying the temperature and pressure of the system until critical opalescence is observed.

In FIG. 1 is shown a plot of mixtures of hydrogen chloride and n-hexane. The axis of abscissas represents temperature in degrees centigrade and the axis of ordinates represents pressures in pounds per square inch absolute (psia). The curve line represents the critical temperature and critical pressure of mixtures of varying proportions of hydrogen chloride and n-hexane. For this given system, region II, that is, the area defined by points (a), (b), (c) and (d) would be within the temperature and pressure conditions required by the present invention for the given system. Point (b) represents the critical temperature and pressure of 100 percent hydrogen chloride. Point (d) represents the critical temperature and pressure of 100 percent n-hexane. Points from (b) to (c) to (d) represent critical temperatures and pressures of mixtures of varying proportions of hydrogen chloride and n-hexane. It should be noted that the mole fraction of hydrogen chloride in the mixture with n-hexane is a linear function of temperature. Thus, the estimated mole fractions of HCl and n-hexane components at points (b), (c) and (d) of FIG. 1 are as follows:

| Points | $x_{HCl}$ | $x_{C_6}$ |
|---|---|---|
| b | 1 | 0 |
| c | 0.611 | 0.389 |
| d | 0 | 1 | wherein $x$ is the mole fraction.

Point (a) represents the critical temperature of hydrogen chloride and the critical pressure of n-hexane. Thus for the hydrogen chloride-n-hexane system, region I in FIG. 1 represents an area of supercritical conditions. Area III in FIG. 1 represents a region of subcritical conditions outside the range of conditions required by the present invention. The actual temperatures and pressures will differ depending on the hydrocarbon component used and on the hydrogen halide used.

Figure 2:
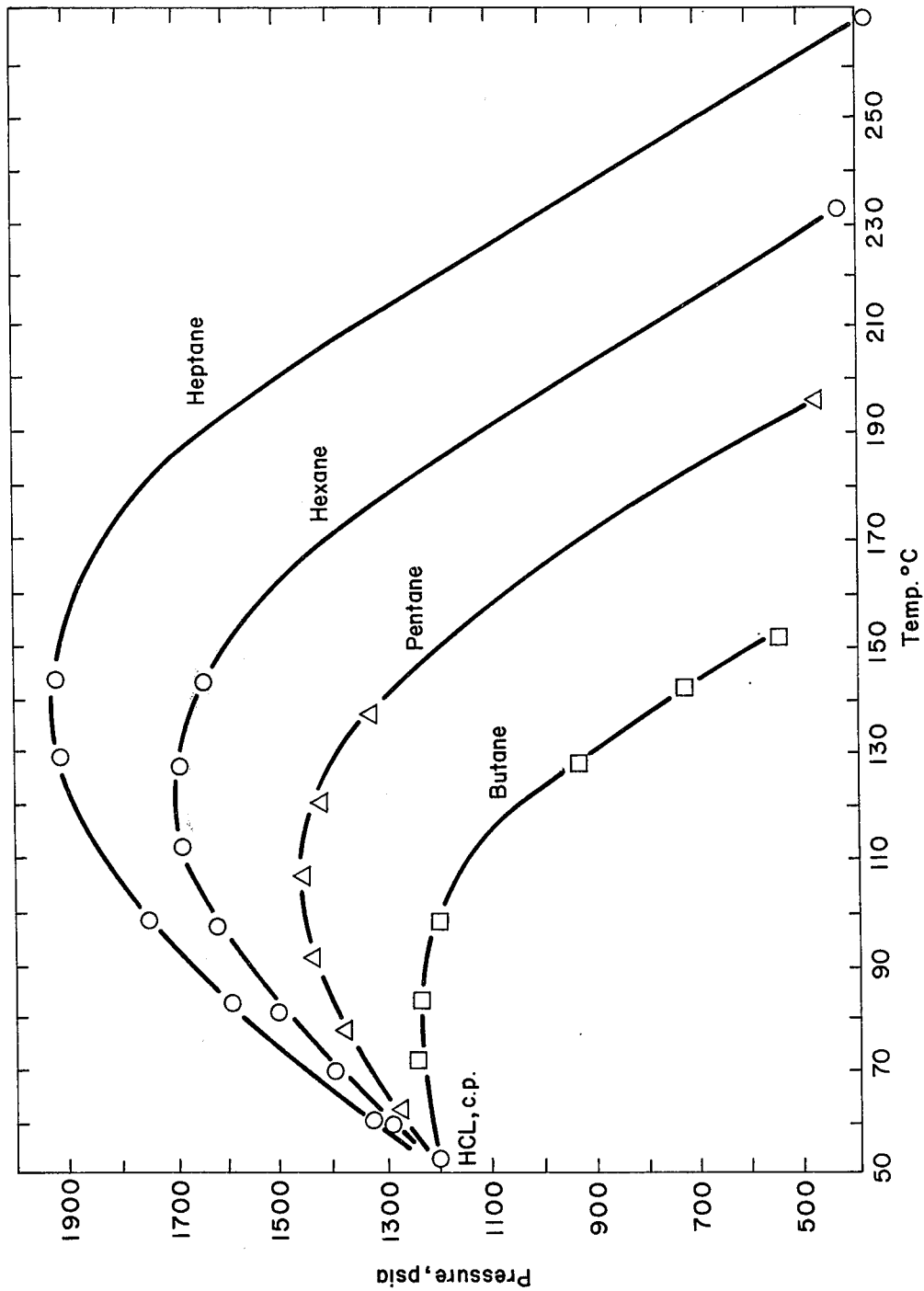
FIG. 2 is a plot showing the critical temperature and pressure of mixtures of hydrogen chloride and different hydrocarbons.

FIG. 2 shows a plot of critical temperature and critical pressure for mixtures of hydrogen chloride-n-butane (the temperature and pressure at the maximum point of the curve being 79°C, 1245 psia); hydrogen chloride-pentane (maximum point of the curve being 102.5°C, 1462 psia); hydrogen chloride-hexane (maximum point of the curve being 122°C, 1695 psia); and hydrogen chloride-heptane (maximum point of the curve being 139°C, 1925 psia), respectively. For example, at about 90°C, utilizing a hexane feed, the partial pressure of the mixture of hexane and hydrogen chloride is preferably maintained in the range of about 500 to 1400 psia.

Figure 3:
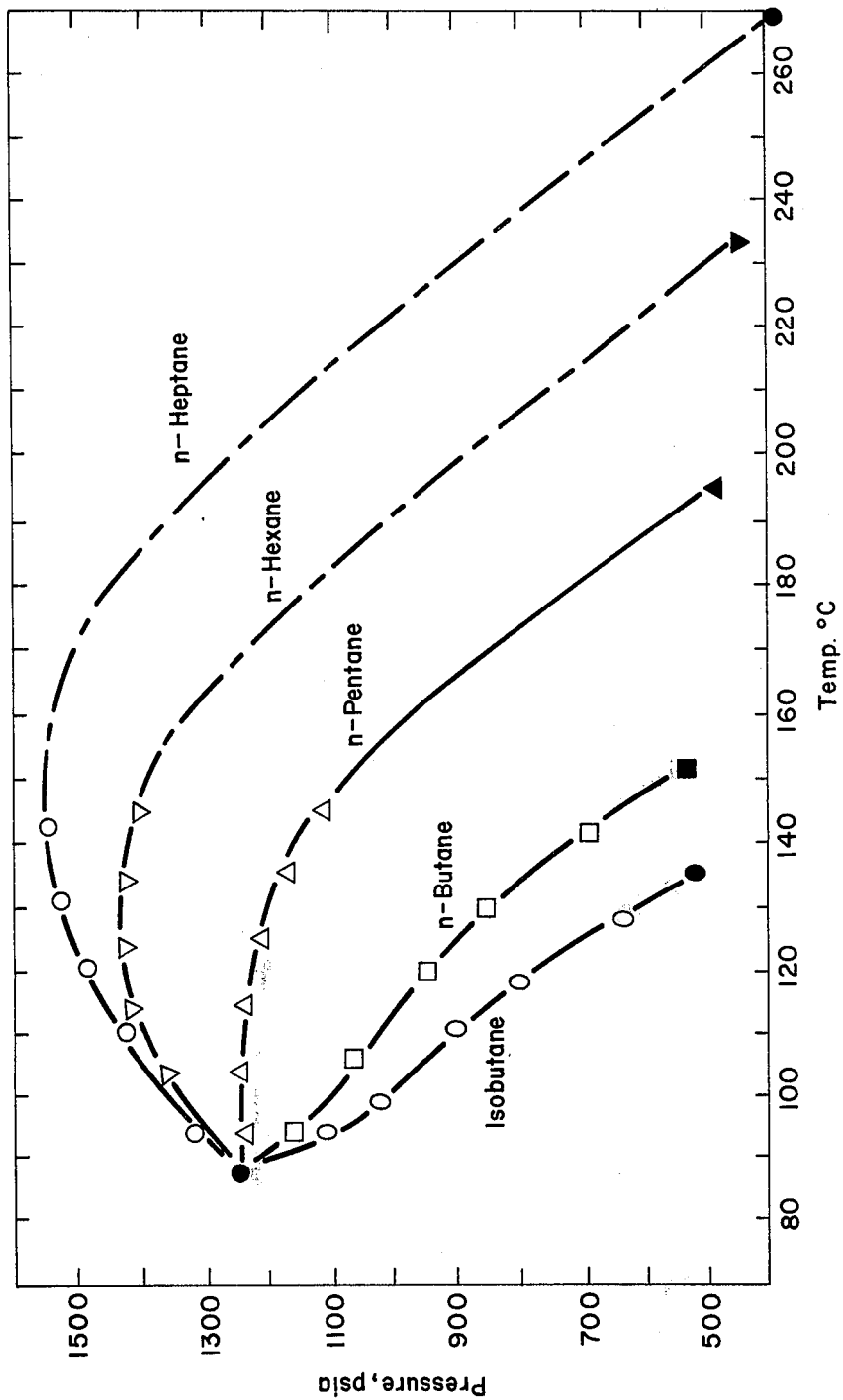
FIG. 3 is a plot showing the critical temperature and pressure of mixtures of hydrogen bromide and different hydrocarbons.

FIG. 3 shows a plot of critical temperature and pressure for mixtures of hydrogen bromide-isobutane (maximum point on curve being 90°C, 1235 psia); hydrogen bromide-n-butane (maximum point on curve being 90°C, 1235 psia); hydrogen bromide-n-pentane (maximum point on curve being 105°C, 1243 psia); hydrogen bromide-n-hexane (maximum point on curve being 125°C, 1425 psia); hydrogen bromide-n-heptane (maximum point on curve being 155°C, 1535 psia), respectively.

EXAMPLE 1

Experiments were conducted to show the criticality of operating at a hydrogen halide to metal halide ratio ranging from 10:1 to 40:1 in the liquid phase conditions defined in accordance with the process of the present invention.

A series of seven runs were made in a 300 ml autoclave by varying the $HCl/AlCl_3$ mole ratio from 80:1 to 10:1 between 55° and 90°C. The runs were made at constant hydrogen pressure of 300 psia with a hydrocarbon to HCl volume ratio of 0.6/1 (60 ml hydrocarbon to 100 ml HCl). The hydrocarbon feed utilized was a blend consisting of 95.6 percent n-hexane and 4.4 percent methylcyclopentane (i.e. 43.0 gm $n-C_6H_{16}$ and 2.00 gm methylcyclopentane).

The operating conditions of the runs are summarized in Table I. In run 1, the initial charge isomerized with a rate constant of 1.27 $hr.^{-1}$. After allowing the reactor to stir overnight, a second, then a third and fourth charge of feed were added to the vessel. In each case the reaction was followed by periodically sampling the vessel and analyzing the products on a conventional gas chromatograph. Runs 1 to 4 and 7 are runs in accordance with the present invention, whereas, runs 5 and 6 are comparative runs.

EXAMPLE 2

This example is presented to demonstrate that hydrogen is required to prevent rapid deactivation of the catalyst when operating at the temperature and pressure conditions in accordance with the process of the present invention.

A series of runs were made in a 300 ml autoclave at 65°C with an $HCl/AlCl_3$ ratio of 40/1 in which the hydrogen partial pressure was set at 0, 100 and 300 psia. The isomerization constant varied from 3.15 $hr.^{-1}$ with no hydrogen present to 0.075 $hr.^{-1}$ with 300 psia hydrogen. The hydrocarbon feed utilized was a blend consisting of 95.6 percent n-hexane and 4.4 percent methylcyclopentane. The operating conditions for these runs (8, 9, 10) are summarized in Table II. Runs 9 and 10 are runs in accordance with the present invention, whereas run 8 is a comparative run.

TABLE II

| RUN | TOTAL PRESSURE, PSIA | $AlCl_3$, MOLE | HCl, ml | $H_2$, PSIA | $C_6$ MIX, ml | T°C | REACTION TIME, MINUTES | K ISO, $HR.^{-1}$ |
|---|---|---|---|---|---|---|---|---|
| 8 | 994.7 | 0.06 | 100 | 0 | 60 | 65°C | 0–33 | 3.15 |
| 9 | 1174.7 | 0.06 | 100 | 100 | 60 | 65°C | 0–339 | 0.26 |
| 10 | 1434.7 | 0.06 | 100 | 300 | 60 | 65°C | 0–1434 | 0.075 |

Results of run 8, in which no hydrogen was present, and which is therefore outside the scope of the present invention, are summarized in Table III.

TABLE III

| $H_2$ Psia | Time, Min. | % $C_5-$ | % $nC_6/C_6$ |
|---|---|---|---|
| 0 | 4 | 0 | 94.3 |
| 0 | 11 | 0.04 | 70.0 |
| 0 | 22 | 0.46 | 47.2 |
| 0 | 33 | 5.68 | 30.4 |
| 0 | 46 | 79.6 | 10.1 |
| 0 | 55 | 85.3 | 4.5 |

As can be seen from the data in Table III, in the

TABLE I

| RUN | TOTAL PRESSURE, PSIA | $AlCl_3$, MOLE | HCL, ml | $H_2$, PSIA | $C_6$ MIX, ml | T,°C | $HCl/AlCl_3$ | K ISO, $HR.^{-1}$ | REACTION TIME, MINUTES |
|---|---|---|---|---|---|---|---|---|---|
| 1 | 1614.7 | 0.06 | 100 | 300 | 60 | 90 | 40/1 | 1.27 | 0–234 |
|  |  |  |  |  | +60 |  |  | 2.30 | 1327–1460 |
|  |  |  |  |  | +60 |  |  | 1.33 | 1530–1576 |
|  |  |  |  |  | +60 |  |  | 1.07 | 1620–1666 |
| 2 | 1734.7 | 0.24 | 100 | 300 | 60 | 90 | 10/1 | 1.84 | 0–71 |
|  |  |  |  |  | +60 |  |  | (0.7–1.5) | 77–142 |
|  |  |  |  |  | +60 |  |  | (0.25–0.10) | 167–1223 |
| 3 | 1254.7 | 0.06 | 100 | 300 | 60 | 55 | 40/1 | 0.04 | 0–1382 |
| 4 | 1274.7 | 0.12 | 100 | 300 | 60 | 55 | 20/1 | 0.03 | 0–4260 |
| 5 | 1234.7 | 0.03 | 100 | 300 | 60 | 55 | 80/1 | 0.06 | 0–171 |
|  |  |  |  |  |  | 65 |  | 0.06 | 171–1333 |
|  |  |  |  |  |  | 75 |  | (.2–.15) | 1333–1733 |
|  |  |  |  |  | +60 | 75 |  | 0.10 | 2804–3018 |
|  |  |  |  |  |  | 90 |  | 0.47 | 3018–3206 |
|  |  |  |  |  | +60 | 90 |  | — | 4249–4349 |
| 6 | 1544.7 | 0.045 | 100 | 300 | 60 | 75 | 60/1 | 0.13 | 0–172 |
|  |  |  |  |  |  | 90 |  | 0.99 | 199–323 |
| 7 | 1434.7 | 0.06 | 100 | 300 | 60 | 65 | 40/1 | 0.08 | 0–1434 |

As can be seen from Table I, when comparing the runs made at 90°C, runs 5 and 6 which were carried out outside the range of HCl to $AlCl_3$ of the present invention showed low isomerization activity.

absence of hydrogen, cracking products developed as the reaction proceeded. In runs 9 and 10, with 100 or 300 psia hydrogen, the cracking reactions were minimized.

What is claimed is:

1. An isomerization process which comprises: contacting in a reaction zone, in the presence of hydrogen, a hydrocarbon feed comprising a saturated aliphatic hydrocarbon, a hydrogen halide selected from the group consisting of hydrogen chloride, hydrogen bromide and mixtures thereof, said hydrocarbon feed and hydrogen halide being substantially in liquid phase, and a metal halide catalyst selected from the group consisting of aluminum chloride, aluminum bromide and mixtures thereof, at a temperature ranging from at least about 50°C. to the critical temperature of the mixture of said hydrocarbon feed and said hydrogen halide, said critical temperature ranging up to about 150°C., the partial pressure of said hydrogen ranging from about 40 to about 1000 psia, the molar ratio of said hydrogen to said hydrocarbon feed ranging from 0.05 to 2.5 moles hydrogen per mole hydrocarbon feed, the partial pressure of the mixture of said hydrocarbon feed and said hydrogen halide being maintained at least equal to the critical pressure of the hydrocarbon feed and not greater than the critical pressure of said mixture of hydrocarbon feed and hydrogen halide, said partial pressure of the mixture of said hydrocarbon feed and said hydrogen halide ranging from about 250 to about 2500 psia, and wherein the molar ratio of said hydrogen halide to said hydrocarbon feed is at least 1:1 and the molar ratio of said hydrogen halide to said metal halide catalyst ranges from about 10:1 to about 40:1.

2. The process of claim 1, wherein said molar ratio of hydrogen halide to metal halide ranges from about 20:1 to about 40:1.

3. The process of claim 1, wherein the molar ratio of said hydrogen halide to said hydrocarbon feed ranges from about 2:1 to about 10:1.

4. The process of claim 1, wherein said hydrocarbon feed comprises a member selected from the group consisting of saturated acyclic hydrocarbons having at least 4 carbon atoms, saturated alicyclic hydrocarbons having at least 6 carbon atoms and mixtures thereof.

5. The process of claim 1, wherein said hydrocarbon feed comprises an acyclic aliphatic hydrocarbon having from 4 to 12 carbon atoms.

6. The process of claim 1, wherein said hydrocarbon feed comprises saturated acyclic aliphatic hydrocarbons having from 4 to 7 carbon atoms.

7. The process of claim 1, wherein said hydrogen halide is hydrogen chloride, said hydrocarbon feed is hexane, said partial pressure of the mixture ranges from about 434 to 1695 psia, and said isomerization is conducted at a temperature ranging from about 50° to about 122°C.

8. The process of claim 1, wherein said hydrogen halide is hydrogen chloride, said hydrocarbon feed is butane, said partial pressure of the mixture ranges from about 551 to 1245 psia, and said isomerization is conducted at a temperature ranging from about 50° to 79°C.

9. The process of claim 1, wherein said hydrogen halide is hydrogen chloride, said hydrocarbon feed is pentane, said partial pressure of the mixture ranges from about 485 to 1462 psia and said isomerization is conducted at a temperature ranging from about 50° to about 102.5°C.

10. The process of claim 1, wherein said hydrogen halide is hydrogen bromide, said hydrocarbon feed is isobutane, said partial pressure of the mixture ranges from about 544 to 1235 psia, and said isomerization is conducted at temperature ranging from about 50° to about 90°C.

11. The process of claim 1, wherein said hydrogen halide is hydrogen bromide, said hydrocarbon feed is n-pentane, said partial pressure of the mixture ranges from about 485 to 1243 psia, and said isomerization is conducted at a temperature ranging from about 50° to about 105°C.

12. The process of claim 1, wherein said hydrogen halide is hydrogen bromide, said hydrocarbon feed is n-hexane, said partial pressure of said mixture ranges from about 434 to 1425 psia, and said isomerization is conducted at a temperature ranging from about 50° to about 125°C.

13. The process of claim 1, wherein said hydrogen halide is hydrogen bromide, said hydrocarbon feed is n-heptane, said partial pressure of the mixture ranges from about 394 to 1535 psia, and said isomerization is conducted at a temperature ranging from about 50° to 155°C.

14. The process of claim 1, wherein said isomerization is conducted at a temperature of about 90°C, said hydrocarbon feed being hexane, said catalyst being aluminum chloride, said hydrogen halide being hydrogen chloride, the partial pressure of the mixture of said hexane and hydrogen chloride being maintained in the range of about 500 to 1400 psia, the partial pressure of said hydrogen ranging from about 40 to 400 psia, said molar ratio of hydrogen chloride to hexane ranging from about 2:1 to about 10:1, and said molar ratio of hydrogen chloride to aluminum chloride ranging from about 20:1 to about 40:1.

15. The process of claim 1 wherein said temperature ranges from about 65° to about 110°C.

16. The process of claim 1 wherein said metal halide catalyst consists essentially of aluminum bromide or aluminum chloride.

* * * * *